United States Patent [19]
Devos et al.

[11] Patent Number: 6,117,457
[45] Date of Patent: Sep. 12, 2000

[54] USE OF PERACETIC ACID IN FISH FARMING

[75] Inventors: Christine Devos, Versailles; Jean-Jack Godin; Catherine Hamon, both of Chatillon, all of France

[73] Assignee: Chemoxal, S.A., Paris, France

[21] Appl. No.: 08/990,987

[22] Filed: Dec. 15, 1997

[30] Foreign Application Priority Data

Dec. 13, 1996 [FR] France .................................. 96 15369
Jan. 9, 1997 [FR] France .................................. 97 00158

[51] Int. Cl.$^7$ .......................... A01N 59/00; A01N 37/16; A01N 61/00; A01N 63/04
[52] U.S. Cl. ........................... 424/616; 514/557; 422/28; 422/29; 119/231; 119/268
[58] Field of Search .......................... 424/616; 514/557; 422/28, 29; 119/231, 268

[56] References Cited

U.S. PATENT DOCUMENTS

| | | | |
|---|---|---|---|
| 4,743,447 | 5/1988 | Le Rouzic et al. | 514/839 |
| 5,313,911 | 5/1994 | Thomassen et al. | 119/231 |
| 5,393,781 | 2/1995 | Vegega et al. | 514/557 |

FOREIGN PATENT DOCUMENTS

| | | |
|---|---|---|
| 193 416 A1 | 9/1986 | European Pat. Off. . |
| 370 850 A1 | 3/1990 | European Pat. Off. . |
| 195 31 241 A1 | 2/1997 | Germany . |
| 2 260 703 | 4/1993 | United Kingdom . |
| 96/03046 | 2/1996 | WIPO . |
| 96/18297 | 6/1996 | WIPO . |

OTHER PUBLICATIONS

"Bactericidal Properties of Peracetic Acid and Hydrogen Peroxide, Alone and in Combination, and Chlorine and Formaldehyde Against Bacterial Water Strains", A. Alasri, et al., Jan. 27, 1992, Canadian Journal of Microbiology.

Database Aquasci, STN–International, STN–Accession No. 97:32266, J.H. Lilley et al., "Comparative Effects of Various Antibiotics, Fungicides and Disinfectants on Aphanomyces Invaderis and Other Saprolegniaceous Fungi", 1997.

Database WPI, Section Ch, Week 9006, Derwent Publications Ltd., London GB; Class B06, AN 90–040628, XP002049273 & JP 01 317 346 A (Katayama Kaeaku Kogyo KE), 1990.

Database WPI, Section Ch, Derwent Publications Ltd., London GB; Class C02, AN 71–67701S, XP002049274 & JP 46 035 867 B (Sogoyakko KK), 1971.

Database WPI, Section Ch, Derwent Publications Ltd., London GB; Class C00, AN 67–00755H, XP002049275 & JP 42 023 242 B (Kokin Chemical Co Ltd), 1968.

Database WPI, Section Ch, Week 8312, Derwent Publications Ltd., London GB; Class A82, AN 83–28342K, XP002049276 & JP 58 023 604 A (Mitsubishi Gas Chem Co. Inc.), 1983.

Database WPI, Section Ch, Week 9644, Derwent Publications Ltd., London GB; Class C03, AN 96–434228, XP002049277 & AU 44407 96 A (Peroxythai Ltd), 1996.

Database WPI, Section Ch, Week 8641, Derwent Publications Ltd., London GB; Class D15, AN 86–269429, & XP002049278 JP 61 197 406 A (Toppan Printing Co Ltd), 1986.

*Primary Examiner*—John Pak
*Attorney, Agent, or Firm*—Burns, Doane, Swecker & Mathis, L.L.P.

[57] ABSTRACT

Process for controlling growth and/or removing parasites from pond water comprising adding to the pond water peracetic acid and hydrogen peroxide, simultaneously or separated in time, in amounts effective to control and/or remove said parasites.

8 Claims, No Drawings

USE OF PERACETIC ACID IN FISH FARMING

BACKGROUND OF THE INVENTION (i) Field of the Invention

The invention relates to controlling the growth of parasites and/or to removing the said parasites in an aquatic environment.

The proliferation of parasites can cause significant damage, in particular in aquacultural breeding ponds. Mention may be made, for example, of *Lepeophtheirus salmonis* K., commonly known as the "sea louse", which is responsible for significant losses in salmon farming. These parasites attach themselves not only to the body of the fish but also to the walls of the breeding ponds.

(ii) Description of the Related Art

Mention may be particularly made, among the treatments described in the state of the art, of those in which the active principle is hydrogen peroxide, as in British Patent Application GB 2,260,703 or Japanese Patent Application JP 010317346.

However, these treatments employ high concentrations of hydrogen peroxide (about 1.5 $g/dm^3$) for contact times which are often greater than 20 minutes.

SUMMARY OF THE INVENTION

Now, the Applicant Company has noticed that, on the one hand, certain species of aquatic animals, in particular fish, endure high concentrations of hydrogen peroxide for only short times and that, on the other hand, hydrogen peroxide does not always have the desired lethal effect on the parasite.

The subject of the invention is thus a process for the treatment of pond water intended to control the growth of parasites and/or to remove the parasites, characterized in that effective amounts of peracetic acid and of hydrogen peroxide are added, simultaneously or separated in time.

Pond denotes any confined region intended to contain water, it being possible for the confinement to be temporary or permanent.

In the case of a permanent confinement, mention may be made, for example, of permanent breeding ponds which are isolated from the natural environment and which are fed with river or sea water by appropriate pumping means; the water thus used can either be discharged into the natural environment or recycled.

In the case of a temporary confinement, mention may be made, for example, of marine cages known to a person skilled in the art, which are equipped at their base with a tarpaulin, the edges of which can be raised in order to obtain a confined region during the implementation of the process according to the invention.

DETAILED DESCRIPTION OF PREFERRED EMBODIMENTS

A particular subject of the invention is the process as described above, employed for treating fish-farming water.

In a preferred alternative form of the present invention, the process as described above is employed for controlling the growth of fish ectoparasites, such as *Caligus spinosus* or *Fugus rubriques*, or that of salmonid parasites, such as *Lepeophtheirus salmonis*, and/or for removing the said parasites.

In a second preferred alternative form of the present invention, the addition is carried out, to the water of the said pond, which can be fresh water or sea water, of the amount of peracetic acid and of hydrogen peroxide necessary in order to obtain a concentration of peracetic acid of between 1 and 10 ppm and a concentration of hydrogen peroxide of between 200 and 900 ppm.

In a third alternative form of the process which is the subject of the present patent application, the addition is carried out, to the water of the pond, instead of the peracetic acid and hydrogen peroxide pair, of a solid formulation which, by dilution in water, produces peracetic acid and hydrogen peroxide and in particular a formulation containing, by weight, from 250 to 3000 parts of tetracetylethylenediamine, from 500 to 5000 parts by weight of sodium perborate or of sodium percarbonate and from 300 to 3000 parts of citric acid.

Such formulations are described in more detail in the international patent application published under the number WO 96/18297. They are used for the implementation of the process according to the invention after, if necessary, being diluted prior to the process.

In a fourth alternative form of the process which is the subject of the present patent application, the addition is carried out, to the water of the pond, of an aqueous solution comprising acetic acid, peracetic acid and hydrogen peroxide.

Such solutions are described, for example, in the European patent applications published under the numbers EP 0,024,219 or EP 0,087,343, EP 0,193,416 or EP 0,370,850. They can also be prepared by mixing a commercial peracetic acid solution, assaying from 2 to 40% by weight of this peracid, with, if necessary, a commercial aqueous hydrogen peroxide solution assaying from 30% to 70% by weight of this peroxide.

In a fifth alternative form of the process according to the invention, the concentration of dissolved oxygen is maintained at a value in the region of 10 $mg/dm^3$ and not exceeding 20 $mg/dm^3$. This concentration is maintained by, for example, sparging oxygen, air or air enriched with oxygen into the water to be treated.

In a sixth alternative form of the process, the concentration of carbon dioxide is controlled, so as to maintain it below the concentration which has a harmful effect on fish.

In a preferred alternative form of the process as described above, the water of the breeding pond is sea water at a temperature of 0° to 30° C.

Another subject of the invention is a composition for the implementation of a method for the therapeutic treatment of fish in fish farms intended to prevent or to treat the damage caused by parasites, characterized in that it produces, by dilution in the water of the fish farm, effective amounts of peracetic acid and of hydrogen peroxide.

The composition according to the invention can be an aqueous solution comprising acetic acid, peracetic acid and hydrogen peroxide, such as a solution described, for example, in the European patent applications published under the numbers EP 0,024,219, EP 0,087,343, EP 0,193,416 or EP 0,370,850; the said aqueous solution can also be prepared from a commercial solution containing from 2 to 40% by weight of peracetic acid, by mixing it, if necessary, with a commercial solution comprising from 30 to 70% by weight of hydrogen peroxide.

The composition according to the invention can also be a solid formulation which generates peracetic acid and hydrogen peroxide and in particular a formulation containing, by weight, from 250 to 3000 parts of tetracetylethylenediamine, from 500 to 5000 parts by weight of sodium perborate or of sodium percarbonate and from 300 to 3000 parts of citric acid, such as, for example, a formulation described in the international patent application published under the number WO 96/18297; such a formulation can, if necessary, be diluted before implementation of the method.

Fish farm denotes any confined region intended to contain water in which fish are raised.

The confinement of the region can be temporary or permanent. In the case of a permanent confinement, mention may be made, for example, of permanent breeding ponds which are isolated from the natural environment and which are fed with river or sea water by appropriate pumping means; the water thus used can either be discharged into the natural environment or recycled. In the case of a temporary confinement, mention may be made, for example, of marine cages known to a person skilled in the art, which are equipped at their base with a tarpaulin, the edges of which can be raised in order to obtain a confined region during the implementation of the process according to the invention.

The composition which is the subject of the present invention is in particular employed for treating trout, such as, for example, river trout (*Salmo trutta*), or salmon, such as Atlantic salmon.

Depending on the stage of growth of the fish and depending on the species of fish itself, the composition is employed in fresh water, water of controlled salinity or sea water.

The temperature of the water in which the subjects to be treated live is generally between 0° C. and 30° C. and more particularly between 10° C. and 20° C.

In a preferred alternative form, the composition according to the invention is employed so as to establish, in the water of the fish farm in which the fish to be treated are found, a concentration of peracetic acid of between 1 and 10 ppm and a concentration of hydrogen peroxide of between 200 and 900 ppm.

In a final aspect of the present invention, the subject of the invention is a process for the nontherapeutic treatment of farmed fish intended to give them an appearance pleasing to the eye which encourages their consumption, characterized in that the fish are left at least once during their growth for a time of less than 1 hour in water comprising between 1 and 10 ppm of peracetic acid and between 200 and 900 ppm of hydrogen peroxide.

In an alternative form of the process, the concentration of dissolved oxygen in the water is maintained in the region of 10 mg/dm$^3$, without exceeding 20 mg/dm$^3$, by sparging with oxygen, with air enriched with oxygen or with air.

In a final alternative form of the process, the concentration of carbon dioxide is controlled, so as to maintain it below the concentration which has a harmful effect on the fish.

The following examples illustrate the invention without, however, limiting it.

A) TEST NO. 1

In Vitro Test

I—Materials and Method

I.1—The copepods

The copepods (*Lepeophtheirus salmonis*) all originate from the estuary of the Jaudy, on the coast of Brittany. They are removed from rainbow trout (*Onchorhyncus mykiss*). During removal, the temperature of the farm water varies between 14° C. and 16° C., the salinity being stable at 3%.

The copepods are removed in the afternoon in buckets containing water from the site and stored in these same buckets overnight while bubbling air through.

I.2. Experimental protocol

13 Beakers are filled with 1 liter of sea water and the temperature and the salinity are recorded.

The copepods removed the day before are distributed in the 13 beakers, at the rate of 12 per beaker, care being taken to choose the most vigorous.

The state of vigour of the copepods in the beakers is observed for 5 minutes and weak individuals are replaced.

Precise amounts of Bactipal®, which is a commercial product, and precise amounts of a commercial hydrogen peroxide solution are introduced into the beaker under consideration in order to reach the desired concentrations of hydrogen peroxide and peracetic acid. The test solution is homogenized by stirring with a Pasteur pipette.

A stopwatch is started in order to define the observation times.

II—Results

The results, represented by the time necessary to obtain 100% mortality of the copepods, are recorded in the following table:

| PAA (ppm)     | 0.0   | 20.0  | 50.0  | 100.0 | 0.0   | 20.0  |
|---------------|-------|-------|-------|-------|-------|-------|
| H$_2$O$_2$ (ppm) | 700.0 | 700.0 | 700.0 | 700.0 | 500.0 | 500.0 |
| Time (minutes)| 20.0  | 10.0  | 10.0  | 10.0  | 60.0  | 20.0  |
| PAA (ppm)     | 20.0  | 50.0  | 0.0   | 37.5  | 75.0  | 100.0 | 200.0 |
| H$_2$O$_2$ (ppm) | 400.0 | 400.0 | 300.0 | 300.0 | 300.0 | 60.0  | 50.0  |
| Time (minutes)| 20.0  | 20.0  | 60.0  | 20.0  | 5.0   | 5.0   | 5.0   |

They demonstrate the intrinsic parasiticidal activity of peracetic acid.

B) TEST NO. 2

The in vitro activity of peracetic acid and hydrogen peroxide solutions on *Lepeophtheirus salmonis*, at non-toxic concentrations for trout, was observed after 30 minutes and 90 minutes of contact; the results are presented in the following table:

| Composition Nos. | 1 | 2 | 3 | 4 | 5 | 6 |
|---|---|---|---|---|---|---|
| PAA (ppm) | 1 | 1 | 1 | 1 | 5 | 5 |
| H$_2$O$_2$ (ppm) | 250 | 200 | 150 | 100 | 250 | 200 |
| % mortality at 30 min | ~40% | ~20% | ~5% | ~15% | ~60% | 15% |
| % mortality at 90 min | 95% | ~40% | ~10% | ~20% | ~90% | 25% |

| Composition Nos. | 7 | 8 | 9 | 10 | 11 | 12 |
|---|---|---|---|---|---|---|
| PAA (ppm) | 5 | 5 | 10 | 10 | 10 | 10 |
| H$_2$O$_2$ (ppm) | 150 | 100 | 250 | 200 | 150 | 100 |
| % mortality at 30 min | ~15% | ~10% | 100% | 35% | — | 18% |
| % mortality at 90 min | 30% | ~30% | 100% | 65% | — | 45% |

These results, obtained in particular for Composition Nos. 1, 5, 9 and 10, demonstrate their activity at concentrations which are non-toxic for trout.

C) TEST NO. 3

In Vivo Test on River Trout

Three substances were tested in 55 liter PVC tanks filled with sea water in which were found 11 trout (100 to 150 g)

The sea water has a stable salinity of 320% at a temperature of 11.5° C.

The 40 river trout, stored in sea water in an open circuit, are deprived of food for 48 hours before the experiment (11 per tank).

On the day of the experiment, the water supply is cut off, the volume is adjusted to 50 l and the air continues to be bubbled through. The substances are introduced using a glass tablet bottle. After the addition, stirring is carried out with a spatula, in addition to the movement of the fish.

After a precise contact time for each substance, circulation of water is reestablished in the tanks at the rate of 2 renewals per hour.

The substances tested are as follows:

| $H_2O_2$ | 200 ppm | 250 ppm | 300 ppm |
|---|---|---|---|
| PPA | | | |
| 1 ppm | | | dynamic 1 h |
| 2 ppm | | dynamic 45 min | |
| 3 ppm | dynamic 30 min | | |

After 4 hours, no mortality is found. No external wounds are observed.

These results demonstrate the "in vivo" activity of the compositions according to the invention and their harmlessness with respect to fish.

D) TEST NO. 4 a) Peracetic acid (PAA) and hydrogen peroxide ($H_2O_2$) are poured into a container filled with 600 litres of sea water at 8° C., so as to obtain an initial PAA concentration of 5 ppm and an initial $H_2O_2$ concentration of 750 ppm. Eight salmon weighing approximately 2 to 3 kg are immediately placed in the container and left for 30 minutes, after which time they are returned to sea water.

It was found that 85% of the copepods had been killed by this treatment, without the salmon having been subjected to stress.

b) The same test is carried out with an initial PAA concentration of 5 ppm but with an initial $H_2O_2$ concentration of 1025 ppm; in this case, most of the copepods are destroyed but observation of the salmon shows that they have been subjected to stress; histological analysis reveals a whitening and the presence of haemorrhages in the gills.

What is claimed is:

1. Process for controlling growth and/or removing parasites from pond water comprising adding to the pond water peracetic acid and hydrogen peroxide, simultaneously or separated in time, in amounts effective to control and/or remove said parasites, wherein said effective amount of peracetic acid is between 1 and 10 ppm and said effective amount of hydrogen peroxide is between 200 and 900 ppm.

2. Process according to claim 1, wherein said pond water is fish-farming water.

3. Process according to claim 1, wherein said parasite is a fish ectoparasite or a salmon parasite.

4. Process according to claim 1, further comprising adding acetic acid to the pond water, wherein the peracetic acid, the hydrogen peroxide and the acetic acid are added as an aqueous solution, and wherein the pond water is in a breeding pond.

5. Process according to claim 1, further comprising the step of maintaining a concentration of oxygen dissolved in the water of the pond at between 10 mg/dm$^3$ and 20 mg/dm$^3$.

6. Process according to claim 1, wherein the water of the pond is sea water at a temperature of 0 to 30° C.

7. Process according to claim 3, wherein said fish ectoparasite is *Caligus spinosus* or *Fugus rubriques*.

8. Process according to claim 3, wherein said salmon parasite is *Lepeophtheirus salmonis*.

* * * * *